United States Patent [19]
Sladek

[11] Patent Number: 6,039,042
[45] Date of Patent: Mar. 21, 2000

[54] PORTABLE CHAMBER FOR METERED DOSE INHALER DISPENSERS

[75] Inventor: David T. Sladek, Tucson, Ariz.

[73] Assignee: Thayer Medical Corporation, Tucson, Ariz.

[21] Appl. No.: 09/028,260

[22] Filed: Feb. 23, 1998

[51] Int. Cl.[7] .......................... A61M 11/00; A61M 15/08; A62B 9/02

[52] U.S. Cl. ............... 128/200.23; 128/203.23; 128/203.24; 128/205.24

[58] Field of Search ................... 128/200.23, 203.23, 128/203.24, 205.24, 207.16, 200.14

[56] References Cited

U.S. PATENT DOCUMENTS

| | | | |
|---|---|---|---|
| 2,890,697 | 6/1959 | Van Sickle | 128/201 |
| 3,490,452 | 1/1970 | Greenfield | 128/196 |
| 3,527,242 | 9/1970 | Ansite | 137/102 |
| 3,635,214 | 1/1972 | Rand et al. | 128/208 |
| 3,838,686 | 10/1974 | Szekely | 128/173 |
| 4,030,492 | 6/1977 | Simbruner | 128/145.8 |
| 4,174,712 | 11/1979 | Moren et al. | 128/173 |
| 4,210,155 | 7/1980 | Grimes | 128/727 |
| 4,259,961 | 4/1981 | Chernack et al. | 128/200.18 |
| 4,456,016 | 6/1984 | Nowacki et al. | 128/207.16 |
| 4,470,412 | 9/1984 | Nowacki et al. | 128/200.18 |
| 4,534,343 | 8/1985 | Nowacki et al. | 128/200.23 |
| 4,940,051 | 7/1990 | Lankinen | 128/200.18 |
| 5,012,803 | 5/1991 | Foley et al. | 128/200.23 |
| 5,012,804 | 5/1991 | Foley et al. | 128/200.23 |
| 5,042,467 | 8/1991 | Foley | 128/200.23 |
| 5,165,392 | 11/1992 | Small, Jr. | 128/200.18 |
| 5,178,138 | 1/1993 | Walstrom et al. | 128/200.23 |
| 5,385,140 | 1/1995 | Smith | 128/200.23 |
| 5,427,089 | 6/1995 | Kraemer | 128/200.14 |
| 5,431,154 | 7/1995 | Seigel et al. | 128/200.14 |
| 5,522,380 | 6/1996 | Dwork | 128/200.23 |
| 5,848,588 | 12/1998 | Foley et al. | 128/200.14 |

FOREIGN PATENT DOCUMENTS

| | | |
|---|---|---|
| WO88/02267 | 4/1988 | WIPO . |
| WO88/03419 | 5/1988 | WIPO . |

OTHER PUBLICATIONS

"Relative Volumes of Respirable Drug Particles Delivered by the ACE™ MDI Spacer as Compared to Other MDI Delivery Devices", by David C. Robson and Ronald N. McHenry, 6 pages.

Instrumentation Industries Inc. product information for Metered Dose Inhaler Adapters, 3 pages.

Monaghan Medical Corporation product information for the AeroVent Aerosol Delivery System, 2 pages.

*Primary Examiner*—John G. Weiss
*Assistant Examiner*—Todd M. Martin
*Attorney, Agent, or Firm*—Cahill, Sutton & Thomas P.L.C.

[57] ABSTRACT

A medication inhalation apparatus for use with an MDI inhaler includes an elongated housing for receiving a plume of medication particles ejected by the MDI inhaler, a mouthpiece, and an inhalation valve disposed between the mouthpiece and the housing. An exhalation valve in the mouthpiece allows exhalation through the mouthpiece, presenting very little resistance to the exhalation effort of the patient. An adapter receives and stabilizes a mouthpiece of the MDI inhaler. The inhalation valve includes an inhalation membrane hanging adjacent to a valve seat. Exhalation into the mouthpiece presses the inhalation membrane against the valve seat, forcing exhaled gas through the exhalation valve. Inhalation causes the inhalation membrane to swing away from the valve seat and mostly out of a path of the medication plume. Impaction of medication particles against the inhalation membrane is avoided, and very little resistance is presented to the inhalation effort of the patient.

15 Claims, 4 Drawing Sheets

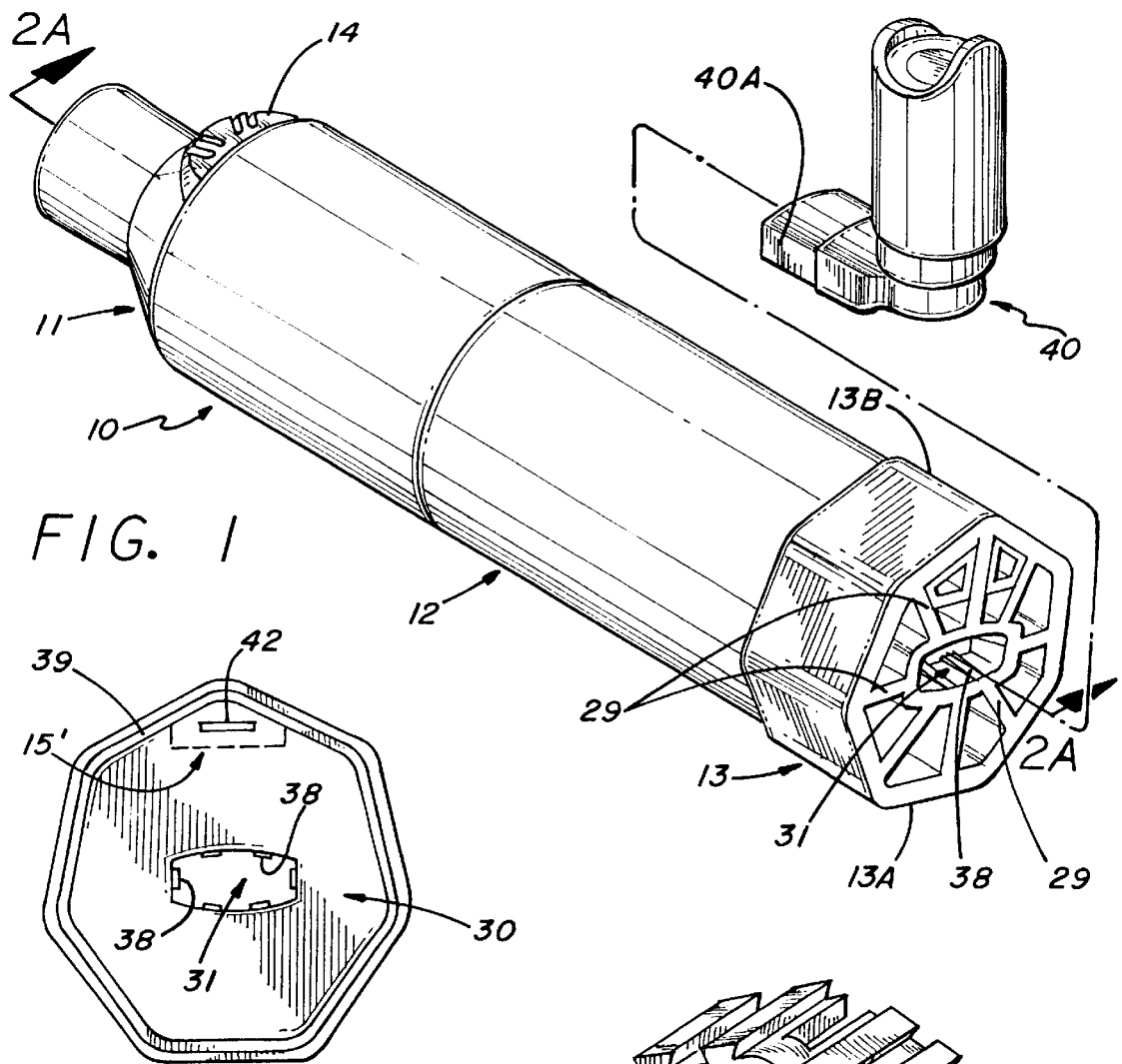
FIG. 1
FIG. 3
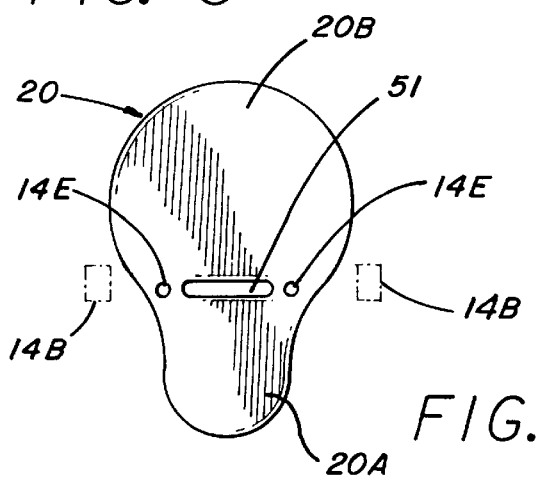
FIG. 4
FIG. 5

PORTABLE CHAMBER FOR METERED DOSE INHALER DISPENSERS

BACKGROUND OF THE INVENTION

The invention relates to a means of delivering aerosol medication from an MDI canister in a dispenser ("boot") supplied by the manufacturer to a patient, through a hand-held chamber operated by the patient.

MDI drug canisters, which have been used since 1956, are sold with a "boot" that includes an actuator, a nozzle, and a mouthpiece. The patient can self-administer the MDI drug using the boot alone; however, the patient must place the mouthpiece of the boot in or near his/her mouth and inhale exactly when the MDI canister is actuated.

For well over a decade various suppliers have provided valved chambers that can be used in conjunction with an MDI boot. Such valved chambers may improve drug delivery by reducing the oropharyngeal deposition of the aerosol drug and by making the synchronization of actuation of the MDI canister and inhalation of the ejected medication less critical.

The most commonly used valved chamber of this type is marketed under the trademark "AEROCHAMBER", is manufactured by Monaghan Medical Corporation, and refers to U.S. Pat. Nos. 4,470,412 and 5,012,803. Another similar valved chamber of this type is marketed under the trademark "OPTICHAMBER", described in U.S. Pat. 5,385,140 (Smith).

The prior AEROCHAMBER device utilizes only an inhalation valve, and the patient must exhale before placing the device in his/her mouth. That presents a significant problem because it is difficult for many patients to initially perform the required sequence of (1) exhaling, (2) then immediately placing the chamber mouthpiece in his/her mouth, (3) then actuating the MDI canister to inject a medication plume into the valved chamber, (4) then taking a slow deep breath and holding his/her breath for a few seconds. The prior OPTICHAMBER device provides both an inhalation valve and an exhalation valve so that the device need not be removed from the patient's mouth in order to use it. Exhaled air effectively "leaks" around the perimeter of a valve membrane. The valve membrane has cross slits that widen as the patient inhales. A problem with the OPTICHAMBER valved chamber is that it is very inefficient in delivering a medication dose to the patient, because even though the chamber is significantly larger than that of the AEROCHAMBER device, an excessive amount of effort is required for some patients to inhale strongly enough to adequately open the cross slit valve and receive an effective medication dose.

It is very desirable that both the inhalation valve and the exhalation valve of a chamber present very little resistance, especially for infants wherein multiple breaths are needed to inhale an effective dose of MDI medication. It also is important that the dead volume, i.e., the space between the valve seat and the mouth opening, be small so that very little air is re-breathed during the multiple breaths that may be needed by an infant to inhale an effective medication dose.

The prior valved chamber devices include elastomeric boot-adapters into which the mouthpiece of the MDI inhaler is inserted. Such boot-adapters have a radially ribbed structure internal to the valved chamber. When the valved chamber is taken apart for cleaning, it is difficult to remove all water used in cleaning from corners formed by the ribs. Consequently, when the valved chamber is reassembled, the presence of such water creates humidity within the valved chamber. Such humidity tends to prevent medication particles ejected from the MDI canister from becoming completely dry (and hence light in weight), as is necessary for optimum transporting of the medication particles into the lungs of the patient. Another problem is that the prior boot-adapters do not sufficiently maintain the MDI inhaler stable as its canister is actuated by the patient. The MDI inhaler device and nozzle therefore become tilted relative to the valved chamber, ejecting the medication plume directly against an interior wall of the valved chamber, resulting in a major loss of medication particles from the plume.

Thus, there is an unmet need for an improved valved chamber device which avoids the above mentioned problems of the prior art and provides a portable, light, reliable, easy-to-use valved chamber for use with MDI inhalers.

SUMMARY OF THE INVENTION

Accordingly, it is an object of the invention to provide a valved chamber which minimizes impacting of medication particles on an inhalation valve membrane.

It is another object of the invention to provide an improved adapter in a valved chamber for receiving the mouthpiece of an MDI boot.

It is another object of the invention to avoid humidity and resulting growth of bacteria in a valved chamber due to difficulty of thoroughly drying the entire inner surface area after cleaning.

Briefly described, and in accordance with one embodiment thereof, the invention provides an elongated housing for receiving a plume of medication particles ejected by an MDI inhaler, having a medication inlet end and a medication outlet end, a mouthpiece connected to the medication outlet end, a one-way inhalation valve disposed between the mouthpiece and a first volume bounded by the housing for allowing flow of gas from the first volume to the mouthpiece, a one-way exhalation valve disposed in the mouthpiece for allowing flow of gas from within the mouthpiece to ambient atmosphere outside of the apparatus, an adapter connected to the medication inlet end for receiving and stabilizing a mouthpiece of the MDI inhaler, wherein the one-way inhalation valve includes an inhalation membrane hanging adjacent to a valve seat. An exhalation by a patient into the mouthpiece presses the inhalation membrane against the valve seat to prevent flow of exhaled gas from the mouthpiece into the volume, causing the exhaled gas to flow from the mouthpiece through the one-way exhalation valve. An inhalation from the mouthpiece by the patient causes the hanging inhalation membrane to swing away from the valve seat and mostly out of a path of flow of gas from the volume into the mouthpiece. The wall is inclined, so the membrane rests on the valve seat when no inhalation or exhalation is occurring. In the described embodiment, the inhalation valve and the exhalation valve comprise a single membrane including the inhalation membrane as a first portion and also including an exhalation membrane as a second portion. The adapter is composed of elastomeric material having a central opening for receiving the mouthpiece of a variety of MDI inhalers. A plurality of generally radial ribs extend between a rim of the adapter and a tube forming the central opening to stabilize the central opening to minimize inadvertent tilting of the MDI inhaler when it is actuated.

BRIEF DESCRIPTION OF THE DRAWINGS

FIG. 1 is a perspective elevation view of the valved chamber of the present invention and a metered dose inhaler for use therewith.

FIG. 2A is a section view of the valved chamber shown in FIG. 1, with a metered dose inhaler shown in dotted lines.

FIG. 2B is a partial section view diagram showing inhalation using the valved chamber of FIG. 1.

FIG. 2C is a partial section view diagram showing exhalation using the valved chamber of FIG. 1.

FIG. 3 is a left side elevation view of the elastomeric boot adapter 13 of FIG. 1, showing the inner surface thereof.

FIG. 4 is a perspective view of a whistle device inserted into the open end of the main chamber as shown in FIG. 1.

FIG. 5 is a plan view of the unitary valve membrane 20 shown in FIGS. 2A–C.

DETAILED DESCRIPTION OF THE PREFERRED EMBODIMENTS

Figure 6:
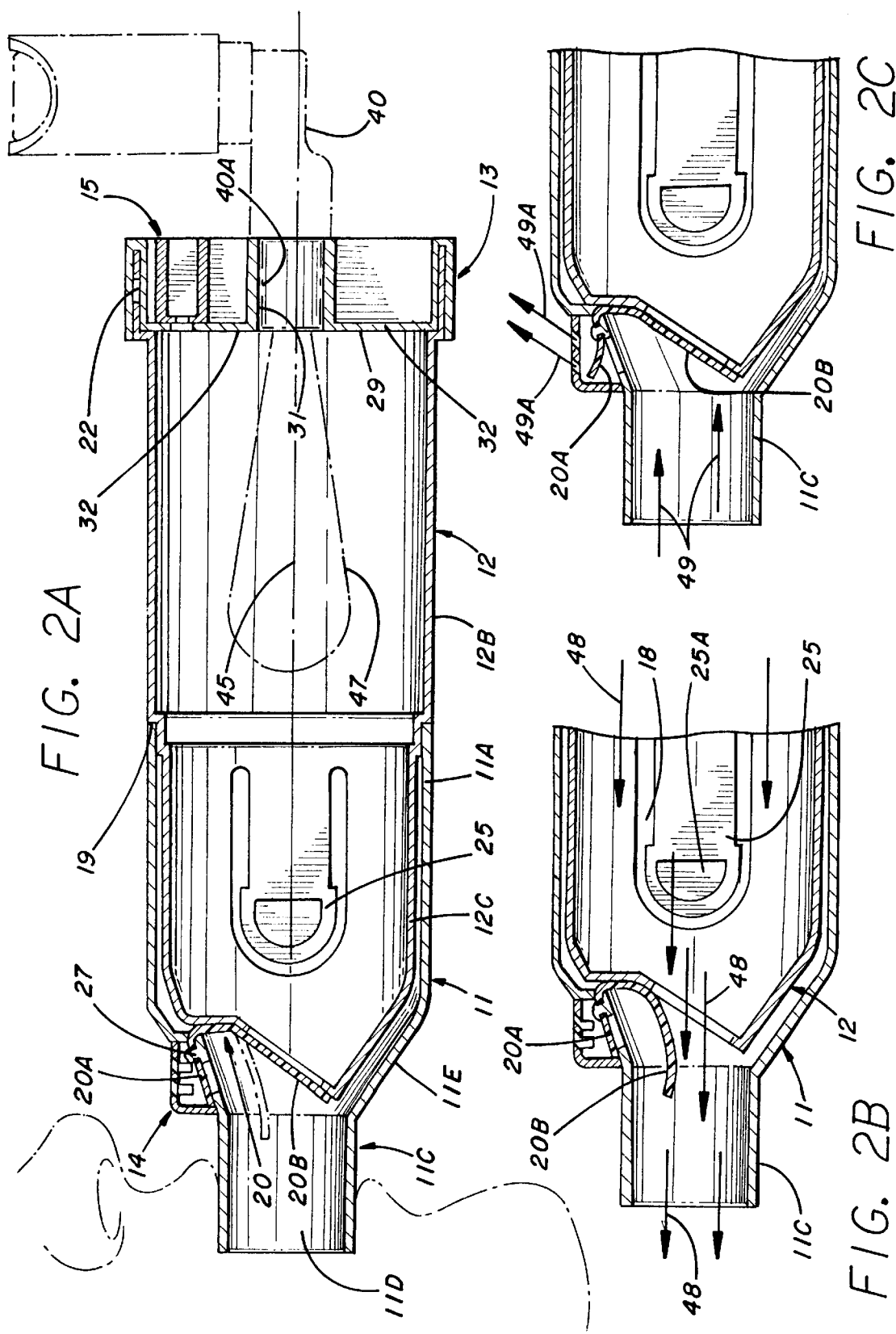
FIG. 6 is an exploded perspective view of the valved chamber device shown in FIG. 1.

Referring to the drawings, valved chamber 10 includes a rigid mouthpiece section 11, a rigid main chamber 12, an elastomeric boot-adapter 13, and a rigid membrane housing 14. Mouthpiece section 11, main chamber 12, and valve membrane housing 14 all can be molded plastic parts composed of transparent plastic, such as ABS plastic or polycarbonate. Boot-adapter 13 can be composed of opaque elastomeric material such as thermoplastic elastomer (TPE) marketed under the trademark KRATON by Shell Chemical Company.

Mouthpiece section 11 includes an enlarged part 11A (FIG. 6) that snap-fits snugly over a nose section 12C of main chamber 12. Tab 25 in U-shaped cutout 18 of main chamber 12 has therein a boss 25A (FIG. 6) that snaps into a mating recess 28 in the inner wall of mouthpiece section 11 when the circular outer edge 11B of mouthpiece 11 abuts an annular shoulder 19 of main chamber 12. Mouthpiece section 11 also includes an intermediate part 11E that tapers down to a reduced diameter section 11C through which a main passage 11D extends. Section 11C usually is inserted into the patient's mouth (See FIG. 2A) or an inhalation mask prior to actuating an MDI inhaler 40 (FIGS. 1 and 2A). When the patient simultaneously inhales and actuates the inhaler 40, a plume 47 of medication particles (FIG. 2A) is ejected approximately symmetrically about longitudinal axis 45. Plume 47 then is available to be immediately carried by the inhalation through mouthpiece opening 11D into the patient's mouth, trachea, and lungs, as subsequently explained.

Removable elastomeric boot-adapter 13 fits tightly on the right open end of main chamber, 12 as shown. The mouthpiece 40A of MDI inhaler 40 fits snugly into central passage 31 of elastomeric boot-adapter 13. Longitudinal ribs 38 and radial spokes 29 perform the function of accommodating the mouthpiece 40A of inhaler 40. The elastomeric material forms a wall 32 (FIG. 2A) with a smooth solid inner surface 30 (FIG. 3) which, together with the eight radial spokes 29, form eight voids. This structure allows the passage 31 to conform to the slightly different dimensions of the mouthpiece of various MDI inhalers and "stabilize" the MDI inhaler to hold it in good alignment with longitudinal axis 45 while the MDI inhaler is being actuated. This prevents medication plume 47 from being inadvertently tilted out of alignment with axis 45 during actuation, and thereby prevents the ejected plume 47 from impinging on the inner sides of main chamber 12.

Referring to FIG. 6, main chamber 12 includes nose section 12C, main body 12B, and a seven-sided rigid flange 21 onto which elastomeric adapter 13 slides. Flange 21 has seven flat surfaces such as 21C arranged as shown. A bottom flat surface of rigid flange 21 is located opposite to a top peak 21B.

At the left upper end portion of main chamber 12 there is a planar, generally semicircular valve seat 12A including three radial spokes 16 defining four pie-shaped passages 17 which open into the interior of main chamber 12. At the opposite end of main chamber 12, a removable whistle element 15 (FIG. 4) is installed to alert the patient if he/she is inhaling too strongly. A barb on whistle 15 is snapped into opening 22 in flange 21.

Elastomeric boot-adapter 13 has seven flat surfaces, including a bottom surface 13A, which are aligned with the seven flat surfaces 21C of flange 21 of main chamber 12 when boot-adapter 13 is installed thereon. Peak 13B (FIG. 1) of boot-adapter 13 is aligned with peak 21B (FIG. 6) of adapter flange 21 of main chamber 12. The flat surfaces 13A on boot-adapter 13 prevent the valved chamber 10 from rolling when it is placed on a surface, so between MDI treatments the patient can leave the MDI inhaler in boot adapter 13, with the boot and MDI canister upright. The peak 13B conveniently indicates the proper orientation of the "top" of valved chamber 10, which is important because right-side-up orientation of the valved chamber 10 improves operation of the inhalation and exhalation membranes 20B and 20A.

As shown in FIG. 6, mouthpiece section 11 includes a valve seat 23 defining a pair of openings 24 which are further defined by a rib 41. A slot 26 in mouthpiece 11 allows an inhale section 20B of a unitary valve membrane 20 (FIG. 5) to extend downward from valve seat 23 of mouthpiece section 11 to rest on valve seat 12A of chamber 12. As shown in FIG. 5, valve membrane 20 includes an exhale section 20A (also referred to as "exhale membrane 20A") and an inhale section 20B (also referred to as "inhale membrane 20B"). An elongated slit 51 in membrane 20 separates exhale and inhale sections 20A and 20B. A hooked retainer 27 (FIGS. 2A–C and 6) extends from valve seat 23 of mouthpiece 11 and passes through narrow slit 51 to maintain the position of exhale membrane 20A on valve seat surface 23 and the position of inhale membrane 20B on valve seat surface 12A. Dotted lines 14B in FIG. 5 show the locations of snap-fit posts that extend from the inner surface of membrane housing 14 to engage receiving slots (not shown) in mouthpiece section 11. Numerals 14E indicate two small posts extending from the inner surface of membrane housing 14 at opposite ends of slit 51 of membrane 20 to a location slightly above valve membrane 20 to prevent it from being accidentally lifted off of boss 27 during exhalation.

Figure 8:
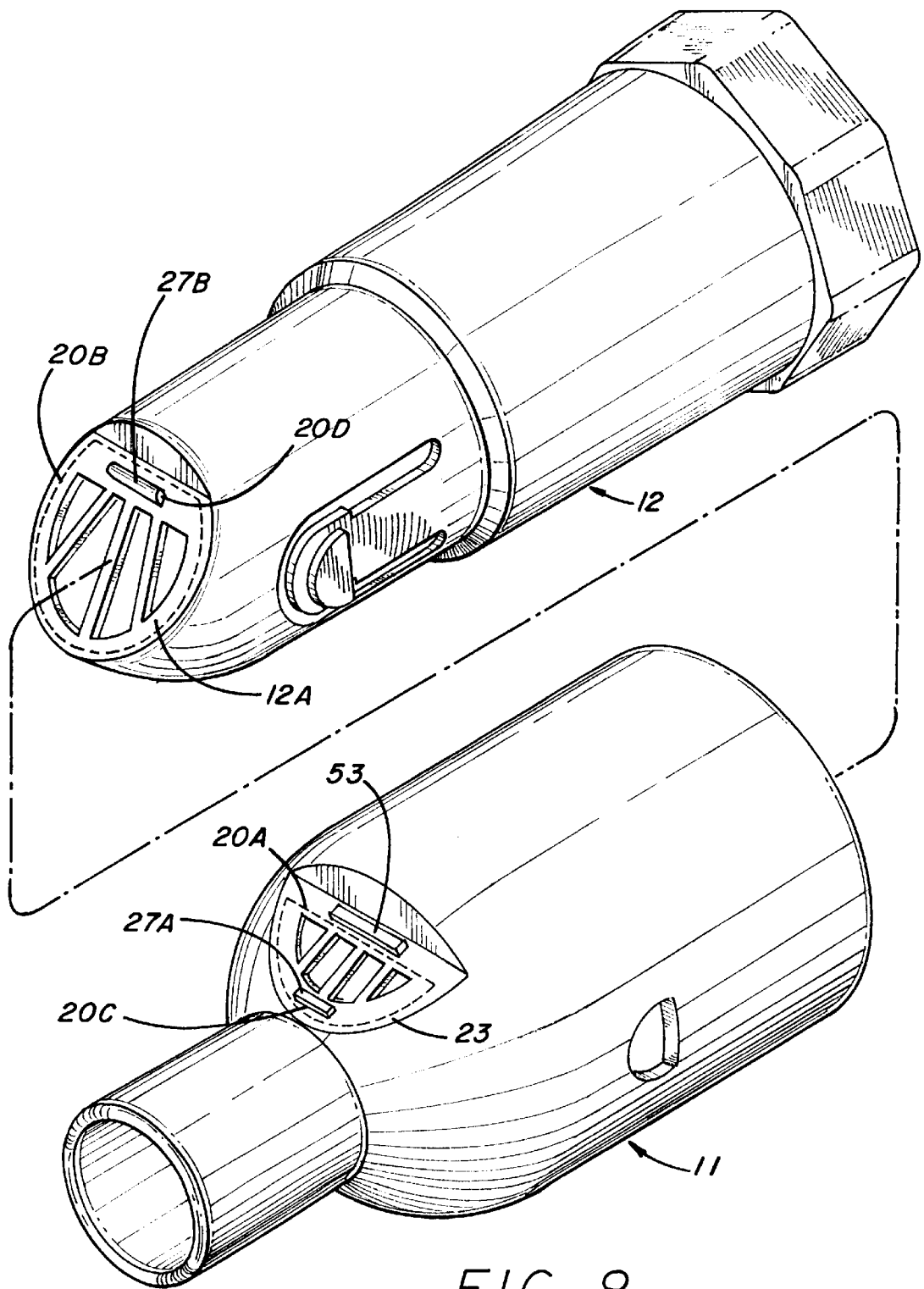
FIG. 8 is an exploded perspective view of an alternative preferred embodiment of the invention.

FIG. 8 shows an alternative preferred embodiment in which exale membrane 20A and inhale membrane 20B are separate. Exhale membrane 20A is hingeably attached to the valve seat 23 by a hooked barb 27A which extends through a slot 20C in exhale membrane 20A. In this embodiment, membrane housing 14 snap fits onto barb 27A and boss 53 over exhale membrane 20A. Inhale membrane 20B is hingeably attached to valve seat 12A by a barb 27A which extends through a slot 20 in inhale membrane 20B. A plastic cap (not shown) may be snap fit onto barb 27B to permanently hold the upper edge of inhale membrane 20B against valve seat 12A.

Figure 7:
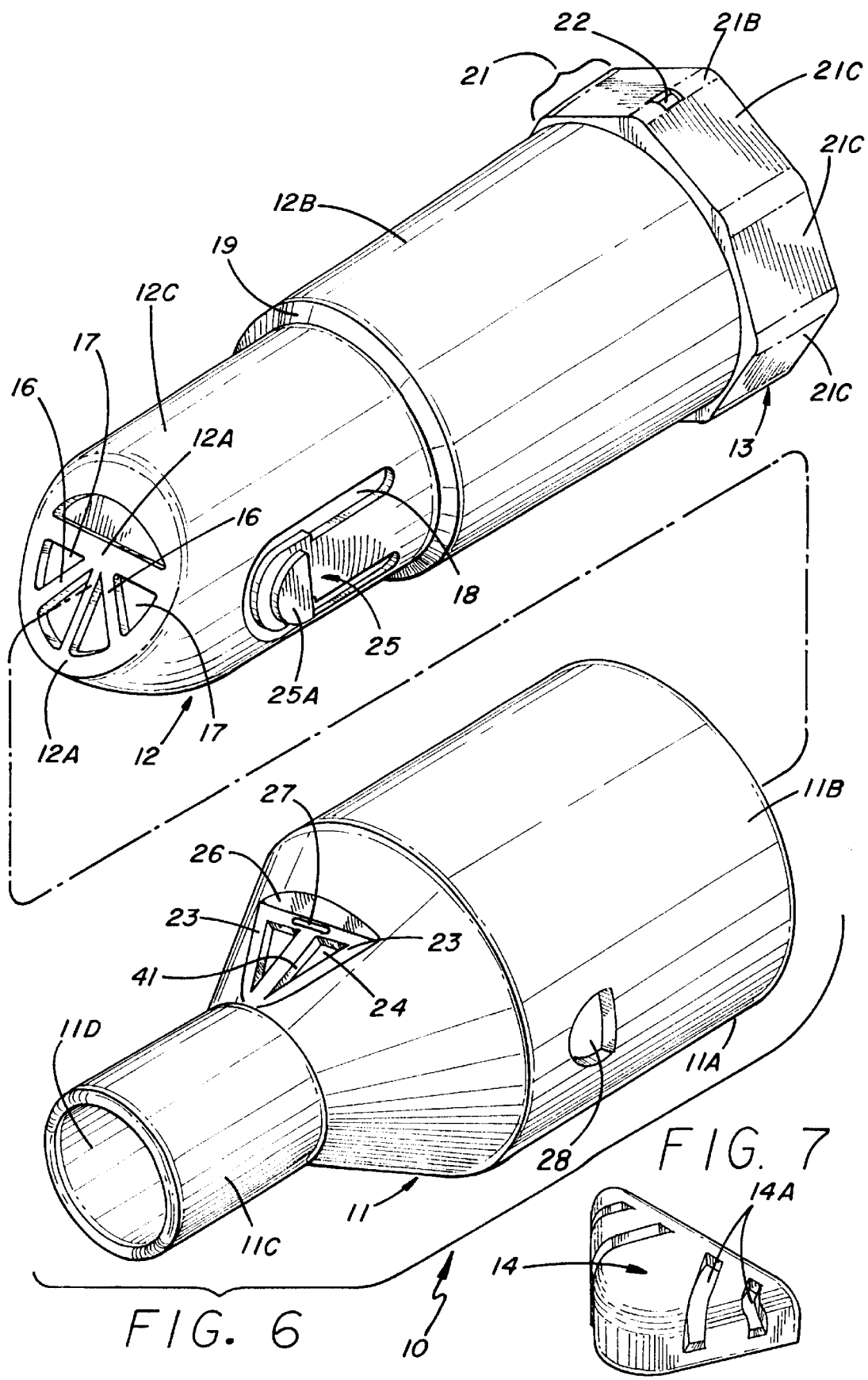
FIG. 7 is a perspective view of the valve membrane housing of the valved chamber shown in FIG. 1.

Preferably, valve membrane 20 is composed of opaque material which is readily visible through the transparent plastic of which valve membrane housing 14, mouthpiece section 11, and main chamber 12 preferably are composed. Exhale membrane 20A rests on valve seat 23 of mouthpiece section 11, and inhale membrane 20B rests on valve seat 12A of main chamber 12. Sections 20A and 20B of valve membrane 20 are connected by an intermediate section positioned as best shown in FIGS. 2A–C. As shown in FIG. 7, membrane housing 14 has a number of vent openings 14A therein to allow exhalation while retaining exhale membrane in place during such exhalation and preventing it from being lifted off of boss 27.

The generally smooth inner surface 30 of boot-adapter 13 is shown in FIG. 3. The inner surface 30 includes continuous peripheral groove 39 that matches the right edge of seven-sided flange 21 (FIG. 6) of main chamber 12. Flange 21 fits into deep groove 39 of boot-adapter 13 when installed on flange 21 of main chamber 12. A hole 42 (FIG. 3) in wall 29 of boot-adapter 13 is aligned with an opening of whistle 15 to allow air to pass through whistle 15, which is installed in flange 21 as illustrated in FIG. 2A. Dotted lines 15' in FIG. 3 indicate the general location of whistle 15 relative to hole 42.

When the person receiving the medication inhales at the same time that medication plume 47 (FIG. 2A) is being ejected by MDI inhaler 40, arrows 48 (FIG. 2B) indicate the flow of air through the pie-shaped openings 17 surrounded by valve seat 12A (FIG. 6) of main chamber 12 and the mouthpiece exhalation openings 24 in mouthpiece section 11. The inhalation air flow 48 lifts inhale membrane 20B from valve seat 12A as shown in FIG. 2B. (The very light weight of hanging flexible inhale membrane 20B is all that normally keeps inhale membrane section 20B resting on valve seat 12A.) Therefore, inhale membrane 20B presents very little resistance to the effort required by the patient to inhale the air flow 48 as it carries medication plume 17 through main chamber 12 and mouthpiece section 11. Furthermore, the drug-laden medication plume 47 moves through the large passage created by the lifting of inhale section 20B of membrane 20, with relatively few of the medication particles of plume 47 impacting the inhale membrane section 20B because it is raised above the flow path of most of medication plume 47. This is in contrast to the above described prior art inhalation valves, in which a substantial portion of the medication plume impacts the valve membrane, and hence does not reach the desired therapeutic sites in the lungs of the patient.

When the patient exhales as indicated by arrows 49 in FIG. 2C, inhale membrane 20B is pressed onto valve seat surface 12A surrounding the openings 17 in main chamber 12. This prevents any of the exhaled air from flowing back into main chamber 12, and deflects the path of the exhaled air 49 through openings 24 surrounding valve seat surface 23 of mouthpiece section 11, as indicated by arrows 49A. This lifts exhale membrane 20A of valve membrane 20 as shown, allowing the exhaled air to escape through the vent openings 14A of valve membrane housing 14 with very little resistance to the patient's exhale effort.

The invention provides an improved valved chamber in which the inhalation flap swings substantially out of the air path as the patient inhales, unlike the slit valves in prior art. The resulting larger opening for the drug-laden air flow 48 to pass by raised inhalation membrane 20B increases the amount of MDI drug delivered to the patient's lungs, in comparison with prior valved inhalation chambers. The inhalation membrane 20B presents very little resistance to the air flow 48, and therefore requires very little inhalation effort by the patient. The exhalation membrane 20A presents very low resistance to airflow 49A, so the patient is not so likely to feel a need to remove the chamber from his/her mouth during the exhalation that precedes actuation and inhalation. Most patients can easily synchronize inhalation with actuation of the MDI canister, because of the fewer number of steps that the patient must coordinate during the critical few seconds while the medication is being delivered, especially if the mouthpiece 11 and membrane housing 14 are transparent and the membrane 20 is opaque so the patient can easily see exactly what is happening inside.

Boot-adapter 13 has its radial spokes 29 on its outer surface, the inner surface 29 of the adapter being flat and smooth. The smooth inner surface 29 is easy to clean, and easy to dry after cleaning. Any water trapped by the corners of radial spokes 29 after cleaning is not within the chamber and therefore does not cause humidity therein, thus preventing bacteria from growing inside main chamber 12.

Thus, the invention provides an improved valved chamber which also provides very low resistance to both inhalation and exhalation by the patient, and provides an inhalation valve membrane which moves almost entirely out of the path of the inhaled medication plume. This prevents impacting of dry medication particles on the inhalation valve membrane, which results in higher effective dry medication doses being delivered to the therapeutic sites in the lungs of the patient. The valved chamber device also can be used effectively to administer an MDI medication dose to an infant because of its ease of inhaling and exhaling.

While the invention has been described with reference to several particular embodiments thereof, those skilled in the art will be able to make the various modifications to the described embodiments of the invention without departing from the true spirit and scope of the invention. It is intended that all elements or steps which are insubstantially different or perform substantially the same function in substantially the same way to achieve the same result as what is claimed are within the scope of the invention.

For example, the mouthpiece and the main chamber could be unitary. A non-elastomeric boot adapter could be integral or partly integral with the main chamber. The exhalation valve could be separate from and quite different in construction from the inhalation valve. Instead of being flexible, the inhalation valve membrane could be a rigid, hinged membrane.

What is claimed is:

1. A medication inhalation apparatus for use with an MDI inhaler, comprising in combination:

a housing for receiving a plume of medication particles ejected by an MDI inhaler;

a mouthpiece connected to one opening of the housing;

a one-way inhalation valve disposed between the mouthpiece and the housing for allowing flow of gas from the housing to the mouthpiece;

a one-way exhalation valve connected to the mouthpiece for allowing flow of gas from within the mouthpiece to ambient atmosphere;

an adapter connected to another opening of the housing for receiving a mouthpiece of the MDI inhaler;

a longitudinal axis extending between the other opening and the mouthpiece, the longitudinal axis forming a path along which inhaled air travels symmetrically from the other opening through the mouthpiece;

the one-way inhalation valve including an inhalation membrane and a valve seat, an exhalation by a patient through the mouthpiece pressing the inhalation membrane against the valve seat to prevent flow of exhaled gas from the mouthpiece into the housing, the exhaled gas flowing through the one-way exhalation valve, inhalation through the mouthpiece causing the inhalation membrane to swing away from the first valve seat and substantially out of a substantially straight-line path of flow of gas along the longitudinal axis from the first volume into the mouthpiece.

2. A medication inhalation apparatus for use with an MDI inhaler, comprising in combination:

an elongated housing for receiving a plume of medication particles ejected by an MDI inhaler, having a medication inlet end and a medication outlet end;

a mouthpiece connected to the medication outlet end;

a one-way inhalation valve disposed between the mouthpiece and the housing for allowing flow of gas from the housing to the mouthpiece;

a one-way exhalation valve connected to the mouthpiece for allowing flow of gas from within the mouthpiece to ambient atmosphere;

an elastomeric adapter connected to the medication inlet end for receiving a mouthpiece of the MDI inhaler;

a longitudinal axis extending between the other opening and the mouthpiece, the longitudinal axis forming a path along which inhaled air travels symmetrically from the other opening through the mouthpiece;

the one-way inhalation valve including an inhalation membrane connected in hinged relationship to a continuous first valve seat, an exhalation by a patient through the mouthpiece pressing the inhalation membrane against the first valve seat to prevent flow of exhaled gas from the mouthpiece into the housing so the exhaled gas flows from the mouthpiece through the one-way exhalation valve, inhalation through the mouthpiece by the patient causing the inhalation membrane to swing away from the first valve seat and substantially out of a substantially straight-line path of flow of gas along the longitudinal axis from the housing into the mouthpiece.

3. The medication inhalation apparatus of claim 2 wherein the housing includes a wall bounding a first volume in the housing and a second volume in the mouthpiece, the first valve seat being disposed on a surface of the wall.

4. The medication inhalation apparatus of claim 3 wherein the wall is inclined relative to a longitudinal axis of the housing, the inhalation membrane resting on the first valve seat when no inhalation is occurring.

5. The medication inhalation apparatus of claim 4 wherein the inhalation membrane is of flexible plastic sheet material having a uniform thickness of approximately 10–12 mils.

6. The medication inhalation apparatus of claim 3 wherein the elongated housing and the mouthpiece are individual units, the elongated housing having a nose section including the wall, the nose section fitting in sealed relationship into an open end of the mouthpiece.

7. The medication inhalation apparatus of claim 3 wherein the inhalation valve and the exhalation valve comprise a unitary membrane including the inhalation membrane as a first portion and an exhalation membrane as a second portion.

8. The medication inhalation apparatus of claim 3 wherein the adapter has a central opening for receiving the mouthpiece of any of a variety of MDI inhalers with mouthpieces having different dimensions.

9. The medication inhalation apparatus of claim 7 wherein the adapter includes a smooth inner surface free of corners and surface irregularities to prevent accumulation of moisture in the first volume after cleaning of the medication inhalation apparatus.

10. The medication inhalation apparatus of claim 9 wherein the adapter includes a plurality of generally radial spokes extending between a peripheral rim of the adapter and a tube forming a central opening of the adapter, the radial spokes stabilizing the tube to minimize inadvertent tilting of the MDI inhaler and the plume ejected thereby.

11. The medication inhalation apparatus of claim 7 wherein the exhalation membrane rests on a continuous second valve seat on an exterior surface of the mouthpiece, whereby exhalation by the patient lifts a portion of the exhalation membrane from the second valve seat, presenting negligible resistance to the exhalation.

12. The medication inhalation apparatus of claim 11 including a vented housing disposed over the exhalation membrane.

13. The medication inhalation apparatus of claim 12 wherein the unitary membrane has an opening therein through which a retainer attached to the mouthpiece extends, the vented housing supporting a post over a portion of the unitary membrane adjacent to the retainer to prevent the unitary membrane from slipping off of the retainer.

14. The medication inhalation apparatus of claim 2 wherein the housing includes a snap fit connector to provide a mouthpiece snap fit connection of the mouthpiece to the housing.

15. The medication inhalation apparatus of claim 12 wherein the mouthpiece, the housing, and the vented housing are transparent, and the inhalation membrane and the exhalation membrane are opaque, to aid patient in learning to use the medication inhalation apparatus.

* * * * *